United States Patent
Heagle

(10) Patent No.: US 9,597,489 B2
(45) Date of Patent: *Mar. 21, 2017

(54) THREE-DIMENSIONAL POROUS FILM CONTACT LAYER WITH IMPROVED WOUND HEALING

(71) Applicant: Smith & Nephew, Inc., Memphis, TN (US)

(72) Inventor: David G. Heagle, Taunton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/087,909

(22) Filed: Mar. 31, 2016

(65) Prior Publication Data

US 2016/0256673 A1  Sep. 8, 2016

Related U.S. Application Data

(63) Continuation of application No. 12/489,883, filed on Jun. 23, 2009.

(Continued)

(51) Int. Cl.
*A61M 1/00* (2006.01)
*A61F 13/00* (2006.01)
(Continued)

(52) U.S. Cl.
CPC ....... *A61M 37/00* (2013.01); *A61F 13/00068* (2013.01); *A61F 13/02* (2013.01);
(Continued)

(58) Field of Classification Search
CPC ........ A61M 1/00; A61M 13/02; A61M 27/00; A61F 13/00; A61B 17/50
See application file for complete search history.

(56) References Cited

U.S. PATENT DOCUMENTS 3,367,332 A  2/1968  Groves
3,486,504 A  12/1969  Austin, Jr.
(Continued)

FOREIGN PATENT DOCUMENTS

DE  41 11 122 A1  4/1993
DE  295 04 378 U1  10/1995
(Continued)

OTHER PUBLICATIONS

US 6,216,701, 04/2001, Heaton et al. (withdrawn)
(Continued)

*Primary Examiner* — Michele M Kidwell
*Assistant Examiner* — Ilya Treyger
(74) *Attorney, Agent, or Firm* — Knobbe, Martens, Olson & Bear, LLP

(57) ABSTRACT

A wound dressing has a micro-architecture to produce appropriate strains in cells to promote the healing a wound. The apparatus includes a wound cover for defining a reservoir over a wound in which a negative pressure may be maintained by forming a substantially fluid-tight seal around the wound, a vacuum source in fluid communication with the reservoir and suitable for providing an appropriate negative pressure to the reservoir to stimulate healing of the wound, and a porous structure positioned in contact with the wound for delivering micro-mechanical forces to localized areas of the wound. The porous structure comprises a three-dimensional film material having directional apertures formed therein.

6 Claims, 3 Drawing Sheets

Related U.S. Application Data

(60) Provisional application No. 61/094,517, filed on Sep. 5, 2008.

(51) Int. Cl.
    *A61M 37/00*     (2006.01)
    *A61F 13/02*     (2006.01)
    *A61N 7/00*     (2006.01)
    *A61M 13/00*     (2006.01)
    *A61M 27/00*     (2006.01)
    *A61B 17/50*     (2006.01)

(52) U.S. Cl.
    CPC ....... *A61F 13/0216* (2013.01); *A61M 1/0023* (2013.01); *A61M 1/0086* (2014.02); *A61M 1/0088* (2013.01); *A61N 7/00* (2013.01); *A61M 2205/058* (2013.01); *A61N 2007/0017* (2013.01)

(56) References Cited

U.S. PATENT DOCUMENTS

| | | |
|---|---|---|
| 3,572,340 A | 3/1971 | Lloyd et al. |
| 3,712,298 A | 1/1973 | Snowdon et al. |
| 3,809,086 A | 5/1974 | Schachet et al. |
| 3,874,387 A | 4/1975 | Barbieri |
| 3,929,135 A | 12/1975 | Thompson |
| 4,080,970 A | 3/1978 | Miller |
| 4,112,947 A | 9/1978 | Nehring |
| 4,112,949 A | 9/1978 | Rosenthal et al. |
| 4,136,696 A | 1/1979 | Nehring |
| 4,266,545 A | 5/1981 | Moss |
| 4,382,441 A | 5/1983 | Svedman |
| 4,508,256 A | 4/1985 | Radel et al. |
| 4,524,064 A | 6/1985 | Nambu |
| 4,710,165 A | 12/1987 | McNeil et al. |
| 4,743,232 A | 5/1988 | Kruger |
| 4,969,880 A | 11/1990 | Zamierowski |
| 4,990,137 A | 2/1991 | Graham |
| 4,997,438 A | 3/1991 | Nipper |
| 5,071,409 A | 12/1991 | Rosenberg |
| 5,100,395 A | 3/1992 | Rosenberg |
| 5,100,396 A | 3/1992 | Zamierowski |
| 5,106,629 A | 4/1992 | Cartmell et al. |
| 5,141,503 A | 8/1992 | Sewell, Jr. |
| 5,149,331 A | 9/1992 | Ferdman et al. |
| 5,152,757 A | 10/1992 | Eriksson |
| 5,160,322 A | 11/1992 | Scheremet et al. |
| 5,176,663 A | 1/1993 | Svedman et al. |
| 5,178,157 A | 1/1993 | Fanlo |
| 5,195,977 A | 3/1993 | Pollitt |
| 5,261,893 A | 11/1993 | Zamierowski |
| 5,263,922 A | 11/1993 | Sova et al. |
| D364,679 S | 11/1995 | Heaton et al. |
| 5,484,427 A | 1/1996 | Gibbons |
| 5,527,293 A | 6/1996 | Zamierowski |
| 5,536,233 A | 7/1996 | Khouri |
| 5,549,584 A | 8/1996 | Gross |
| 5,588,958 A | 12/1996 | Cunningham et al. |
| 5,636,643 A | 6/1997 | Argenta et al. |
| 5,645,081 A | 7/1997 | Argenta et al. |
| 5,678,564 A | 10/1997 | Lawrence et al. |
| 5,701,917 A | 12/1997 | Khouri |
| 5,733,305 A | 3/1998 | Fleischmann |
| 5,779,657 A | 7/1998 | Daneshvar |
| 5,840,049 A | 11/1998 | Tumey et al. |
| 5,911,222 A | 6/1999 | Lawrence et al. |
| 5,944,703 A | 8/1999 | Dixon et al. |
| 6,010,524 A | 1/2000 | Fleischmann |
| 6,071,267 A | 6/2000 | Zamierowski |
| 6,117,111 A | 9/2000 | Fleischmann |
| 6,135,116 A | 10/2000 | Vogel et al. |
| D434,150 S | 11/2000 | Turney et al. |
| 6,142,982 A | 11/2000 | Hunt et al. |
| 6,174,306 B1 | 1/2001 | Fleischmann |
| 6,203,563 B1 | 3/2001 | Fernandez |
| 6,261,276 B1 | 7/2001 | Reitsma |
| 6,325,788 B1 | 12/2001 | McKay |
| 6,345,623 B1 | 2/2002 | Heaton et al. |
| 6,348,423 B1 | 2/2002 | Griffiths et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,458,109 B1 | 10/2002 | Henley et al. |
| 6,488,643 B1 | 12/2002 | Tumey et al. |
| 6,500,112 B1 | 12/2002 | Khouri |
| D469,175 S | 1/2003 | Hall et al. |
| D469,176 S | 1/2003 | Hall et al. |
| 6,520,982 B1 | 2/2003 | Boynton et al. |
| 6,553,998 B2 | 4/2003 | Heaton et al. |
| D475,134 S | 5/2003 | Randolph |
| 6,557,704 B1 | 5/2003 | Randolph |
| D478,659 S | 8/2003 | Hall et al. |
| 6,607,495 B1 | 8/2003 | Skalak et al. |
| 6,626,891 B2 | 9/2003 | Ohmstede |
| 6,648,862 B2 | 11/2003 | Watson |
| 6,685,681 B2 | 2/2004 | Lockwood et al. |
| 6,689,986 B2 | 2/2004 | Patel et al. |
| 6,695,823 B1 | 2/2004 | Lina et al. |
| 6,695,824 B2 | 2/2004 | Howard et al. |
| D488,558 S | 4/2004 | Hall |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,979,324 B2 | 12/2005 | Bybordi et al. |
| 6,994,702 B1 | 2/2006 | Johnson |
| 7,022,113 B2 | 4/2006 | Lockwood et al. |
| 7,037,254 B2 | 5/2006 | O'Connor et al. |
| 7,052,167 B2 | 5/2006 | Vanderschuit |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hanningan et al. |
| 7,169,151 B1 | 1/2007 | Lytinas |
| 7,182,758 B2 | 2/2007 | McCraw |
| 7,195,624 B2 | 3/2007 | Lockwood et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,381,860 B2 | 6/2008 | Gudnason et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,494,482 B2 | 2/2009 | Orgill et al. |

(56) References Cited

U.S. PATENT DOCUMENTS

| | | |
|---|---|---|
| 7,534,927 B2 | 5/2009 | Lockwood et al. |
| 7,569,742 B2 | 8/2009 | Haggstrom et al. |
| 7,612,247 B2 | 11/2009 | Oyaski |
| 7,625,362 B2 | 12/2009 | Boehringer et al. |
| 7,670,323 B2 | 3/2010 | Hunt et al. |
| 7,699,823 B2 | 4/2010 | Haggstrom et al. |
| 7,700,819 B2 | 4/2010 | Ambrosio et al. |
| 7,723,560 B2 | 5/2010 | Lockwood et al. |
| 7,731,702 B2 | 6/2010 | Bybordi et al. |
| 7,776,028 B2 | 8/2010 | Miller et al. |
| 7,846,141 B2 | 12/2010 | Weston |
| 7,896,856 B2 | 3/2011 | Petrosenko et al. |
| 7,909,805 B2 | 3/2011 | Weston |
| 7,910,791 B2 | 3/2011 | Coffey |
| 7,927,318 B2 | 4/2011 | Risk, Jr. et al. |
| 7,976,519 B2 | 7/2011 | Bubb et al. |
| 8,034,037 B2 | 10/2011 | Adams et al. |
| 8,062,272 B2 | 11/2011 | Weston |
| 8,168,848 B2 | 5/2012 | Lockwood et al. |
| 2001/0031943 A1 | 10/2001 | Urie |
| 2001/0043943 A1 | 11/2001 | Coffey |
| 2002/0016577 A1 | 2/2002 | Ohmstede |
| 2002/0143286 A1 | 10/2002 | Tumey |
| 2002/0151836 A1 | 10/2002 | Burden |
| 2002/0161346 A1 | 10/2002 | Lockwood et al. |
| 2003/0078532 A1 | 4/2003 | Ruszczak et al. |
| 2003/0093041 A1 | 5/2003 | Risk, Jr. et al. |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina et al. |
| 2004/0039415 A1 | 2/2004 | Zamierowski |
| 2004/0064111 A1 | 4/2004 | Lockwood et al. |
| 2004/0064132 A1 | 4/2004 | Boehringer et al. |
| 2004/0093026 A1 | 5/2004 | Weidenhagen et al. |
| 2004/0122434 A1 | 6/2004 | Argenta et al. |
| 2004/0167482 A1 | 8/2004 | Watson |
| 2004/0193218 A1 | 9/2004 | Butler |
| 2004/0241213 A1 | 12/2004 | Bray |
| 2004/0249353 A1 | 12/2004 | Risk, Jr. et al. |
| 2004/0260230 A1 | 12/2004 | Randolph |
| 2005/0020955 A1 | 1/2005 | Sanders et al. |
| 2005/0085795 A1 | 4/2005 | Lockwood et al. |
| 2005/0090787 A1 | 4/2005 | Risk, Jr. et al. |
| 2005/0131327 A1 | 6/2005 | Lockwood et al. |
| 2005/0137539 A1 | 6/2005 | Biggie et al. |
| 2005/0147562 A1 | 7/2005 | Hunter et al. |
| 2005/0177190 A1 | 8/2005 | Zamierowski |
| 2005/0182445 A1 | 8/2005 | Zamierowski |
| 2006/0029650 A1 | 2/2006 | Coffey |
| 2006/0039742 A1 | 2/2006 | Cable, Jr. et al. |
| 2006/0100586 A1 | 5/2006 | Karpowicz et al. |
| 2006/0149170 A1 | 7/2006 | Boynton et al. |
| 2007/0005028 A1 | 1/2007 | Risk, Jr. et al. |
| 2007/0014837 A1 | 1/2007 | Johnson et al. |
| 2007/0016152 A1 | 1/2007 | Karpowicz |
| 2007/0021697 A1 | 1/2007 | Ginther et al. |
| 2007/0027414 A1 | 2/2007 | Hoffman et al. |
| 2007/0032754 A1 | 2/2007 | Walsh |
| 2007/0032755 A1 | 2/2007 | Walsh |
| 2007/0032778 A1 | 2/2007 | Heaton et al. |
| 2007/0055209 A1 | 3/2007 | Patel et al. |
| 2007/0066925 A1 | 3/2007 | Gudnason et al. |
| 2007/0178145 A1 | 8/2007 | Chou et al. |
| 2007/0179460 A1 | 8/2007 | Adahan |
| 2007/0225663 A1 | 9/2007 | Watt et al. |
| 2007/0299369 A1 | 12/2007 | Babaev |
| 2008/0071235 A1 | 3/2008 | Locke et al. |
| 2008/0200857 A1 | 8/2008 | Lawhorn |
| 2008/0200906 A1 | 8/2008 | Sanders et al. |
| 2008/0208147 A1 | 8/2008 | Argenta et al. |
| 2008/0234641 A1 | 9/2008 | Locke et al. |
| 2010/0063484 A1 | 3/2010 | Heagle |

FOREIGN PATENT DOCUMENTS

| | | |
|---|---|---|
| EP | 0 020 662 | 7/1984 |
| EP | 358 302 | 3/1990 |
| EP | 0 853 950 | 7/1998 |
| EP | 1 088 569 | 4/2001 |
| EP | 1 219 311 | 7/2002 |
| GB | 1 549 756 | 8/1979 |
| GB | 2 195 255 A | 4/1988 |
| GB | 2 235 877 A | 3/1991 |
| GB | 2 307 180 A | 11/1996 |
| GB | 2 329 127 A | 3/1999 |
| GB | 2 336 546 A | 10/1999 |
| GB | 2 344 531 A | 6/2000 |
| GB | 2 415 908 | 1/2006 |
| SU | 1762940 | 1/1989 |
| WO | WO 80/01139 | 6/1980 |
| WO | WO 80/02182 | 10/1980 |
| WO | WO 84/01904 | 5/1984 |
| WO | WO 89/05133 | 6/1989 |
| WO | WO 90/11795 | 10/1990 |
| WO | WO 92/19313 | 11/1992 |
| WO | WO 93/09727 | 5/1993 |
| WO | WO 94/20041 | 9/1994 |
| WO | WO 96/05873 | 2/1996 |
| WO | WO 00/21586 | 4/2000 |
| WO | WO 03/005943 | 1/2003 |
| WO | WO 03/018098 | 3/2003 |
| WO | WO 03/030966 | 4/2003 |
| WO | WO 03/045492 | 6/2003 |
| WO | WO 03/057070 | 7/2003 |
| WO | WO 03/057307 | 7/2003 |
| WO | WO 03/086232 | 10/2003 |
| WO | WO 03/092620 | 11/2003 |
| WO | WO 03/101508 | 12/2003 |
| WO | WO 2004/018020 | 3/2004 |
| WO | WO 2005/009488 | 2/2005 |
| WO | WO 2006/105892 | 10/2006 |

OTHER PUBLICATIONS

US 7,186,244, 03/2007, Hunt et al. (withdrawn)
International Search Report for PCT/US09/48351, dated Aug. 17, 2009.
Aubrey, D.A. et al., of the Perineal Wound after Proctectomy by Intermittent Irrigation, Arch. Surg., Oct. 1984, 119, 1141-1144.
Bier, A., Hyperemia as a Therapeutic Agent, Ed. Dr. Gustavus M. Blech, A. Robertson & Co., Chicago 1905.
Bucalo et al. "Inhibition of Cell Proliferation by Chronic Wound Fluid." Wound Repair and Regeneration. Miami, 1993. pp. 181-186.
Chardack, et al., "Experimental studies on Synthetic Substitutes for Skin and Their Use in the Treatment of Burns," vol. 155, No. 1 (128-136), 1961.
Edlich, R.F., et al.: "Evaluation of a New, Improved Surgical Drainage System," The American Journal of Surgery, vol. 149, pp. 295-298, Feb. 1985.
Fleischmann, "Vacuum Sealing for Treatment of Problematical Wounds", University Surgical Clinic and Polyclinic—Accident Surgery Department, WundForum Spezial-IHW 94.
Garcia-Rinaldi, R., et al., Improving the Efficiency of Wound Drainage Catheters, Amer. Journ. of Surg., Sep. 1975, 130, 372-373.
Health Technology, Literature R., "Vacuum Assisted Closure Therapy for Wound Care", Health Technology Literature Review (Dec. 2004), 3-59.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
McLaughlan, James, Sterile Microenvironment for Postoperative Wound Care, The Lancet, pp. 503-504, Sep. 2, 1978.
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).

(56) References Cited

OTHER PUBLICATIONS

Renasys EZ System for Negative Wound Therapy, Smith & Nephew announcement, dated Feb. 24, 2009, in 3 pages.
Sames, C.P., Sealing of Wounds with Vacuum Drainage, Br. Med. Journ., Nov. 5, 1977, p. 1223, Correspondence.
Stewart, Joanne, Ph.D., World Wide Wounds—Next generation of products for wound management—2002 (13 pages).
Stoll, "Energetic Remedies—Cupping: Healing Within a Vacuum," https:I/www.suite101.com/article.cfm/ energetic)remedies/74531, Apr. 13, 2005.
Svedman, "A Dressing Allowing Continuous Treatment of a Biosurface," IRCS Medical Science: Biomedical Technology; Clinical Medicine; Surgery and Transplantation, 7, 221 (1979).
Svedman, "A Dressing System Providing Fluid Supply and Suction Drainage Used for Continuous or Intermittent Irrigation," Annals of Plastic Surgery, vol. 17, No. 2, Aug. 1986 (125-133).
Svedman, "Irrigation Treatment of Leg Ulcers," The Lancet, Sep. 3, 1983 (532-534).
Teder and Svedman et al., "Continuous Wound Irrigation in the Pig," Journal of Investigative Surgery, 1990, vol. 3, pp. 399-407.
Tribble, David E. M.D., An Improved Sump Drain-Irrigation Device of Simple Construction, Archives of Surgery New York, pp. 511-513, 1972 vol. 105.
Wu, W.S., et al., Vacuum therapy as an intermediate phase in wound closure: a clinical experience, Eur J Past Surg (2000) 23: 174-177.
Yu A. Davydov, et al., "Bacteriological and Cylological Assessment of Vacuum Therapy of Purulent Wounds", Vestnik Khirurgii, Oct. 1988, (48-52).
Yu A. Davydov, et al., "Concepts for Clinical Biological Management of the Wound Process in the Treatment of Purulent Wounds Using Vacuum Therapy," Vestnik Khirugii, Feb. 1991, 132-135).
Yu A. Davydov, et al., "Vacuum Therapy in the Treatment of Purulent Lactation Mastitis," Russian Journal: Vesnik Khirurgii, Sep. 1986, (66-70).
International Search Report, re PCT Application No. PCT/US09/48351, dated Oct. 28, 2009.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Bjorn, et al., "Irrigation Treatment in Split-thickness Skin Grafting of Intractable Leg Ulcers," Scand J Plast Reconstr Surg 19: 211-213,1985.
Chariker, M.E., et al, "Effective Management of Incisional and Cutaneous Fistulae with Closed Suction Wound Drainage," Contemporary Surgery. Jun. 1989, pp. 59-63, vol. 34.
Fleischmann, et al., Vacuum Sealing: Indication, Technique and Results, Emr J Orthop Surg Tramatol (1995) 5:37-40.
Gorica Zivadinovic, et al., "Vacuum Therapy in the Treatment of Peripheral Blood Vessels," Conference Papers of the 5th Timok Medical Days, Majdanpek, 1986 (161-164).
Jeter, Katherine F., et al., "Managing Draining Wounds and Fistulae: New and Established Methods", Chronic Wound Care, 1990, pp. 240-246.
Kostiuchenok, et al., "The Vacuum Effect in the Surgical Treatment of Purulent Wounds," Russian Journal: Vestnik Khirurgii, Sep. 1986, (18-21).
Meyer, MD., et al., "In Surgery, Medicine and the Specialties a Manual of its Practical Application", Bier's Hyperemic Treatment, Second Revised Edition, W.B. Saunders Company, 1909.
Mulder, GD, et al., "Clinicians' Pocket Guide to Chronic Wound Repair," Wound Healing Publications Second Edition, 1991.
Ryosuke Fujimoro, MD., et al., "Sponge Fixation Method for Treatment of Early Scars," From the Department of Dermatology in the Faculty Medicine, Kyoto University, vol. 42, No. 4, Oct. 1968 (323-326).
Sandén, Göran MD., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).
Svedman, et al., "Staphylococcal Wound Infection in the Pig: Part I. Course," Annals of Plastic Surgery, vol. 23, No. 3, Sep. 1989 (212-218).
Usupov, et al., "Active Wound Drainage," Russian Journal: Vestnik Khirugii, Apr. 1987, (42-45).
Yu A. Davydov, et al., "Vacuum Therapy in treatment of Acute Purulent Diseases of Soft Tissues and Purulent Wounds," Vestnik Khirurgii, (Surgeon's Herald), Medicine Publishers, 1986.

THREE-DIMENSIONAL POROUS FILM CONTACT LAYER WITH IMPROVED WOUND HEALING

CROSS REFERENCE TO RELATED APPLICATION

This application is a continuation application of co-pending U.S. application Ser. No. 12/489,883, filed on Jun. 23, 2009, which claims priority to, and the benefit of, U.S. Provisional Application Ser. No. 61/094,517, filed on Sep. 5, 2008 by Heagle, the entire contents of which are being incorporated by reference herein.

BACKGROUND

1. Technical Field

The present disclosure relates generally to wound healing, and, in particular, relates to methods and devices for the promotion of wound healing through the application of micro-mechanical forces to localized areas of the wound.

2. Background of Related Art

The application of mechanical stresses to a wound has been found to affect healing of the wound. For example, compressive, tensile and shear forces may be applied to a wound to accelerate the natural healing process. Compressive bandages are commonly used for the treatment of venous leg ulcers, or for patients with interstitial edema, which can impair wound healing. Sub-atmospheric pressure applied to wounds such as a pressure sores, ulcers or burns has been found to promote blood flow to the wound area, stimulate the formation of granulation tissue and encourage the migration of healthy tissue over the wound. These techniques tend to apply forces globally or evenly over large areas of the wound or the patient.

It has also been observed that the application of micro-mechanical forces to localized areas of the wound may cause individual cells to react in a manner beneficial for wound healing. Micro-mechanical forces exerted on individual cells can regulate particular cell functions and may even switch on genes that cause cell proliferation. Experimental data suggests that cells subjected from about 10 percent to about 20 percent strain exhibit proliferation rates favorable for wound healing. Accordingly, devices and methods for the application, concentration or regulation of micro-mechanical forces to localized areas of a wound may promote wound healing.

SUMMARY

The present disclosure describes a wound dressing having a micro-architecture to produce appropriate strains in cells to promote the healing of a wound. The apparatus includes a wound cover for defining a reservoir over a wound in which a negative pressure may be maintained by forming a substantially fluid-tight seal around the wound, a vacuum source in fluid communication with the reservoir and suitable for providing an appropriate negative pressure to the reservoir to stimulate healing of the wound, and a porous structure positioned in contact with the wound for delivering micro-mechanical forces to localized areas of the wound. The porous structure comprises a film material having directional apertures formed therein.

The apparatus may include an energy source adapted to deliver energy to the porous structure. The energy source may comprise an ultrasonic horn.

The porous structure may exhibit a male face and an opposite female face, and the porous structure may be positioned such that the male face is in contact with the wound. Alternatively, the porous structure may be positioned such that the female face is in contact with the wound. The directional apertures may be spaced apart by a distance ranging from about 400 microns to about 800 microns, and may be spaced apart by a distance of about 600 microns. The directional apertures may have a diameter ranging from about 50 microns to about 350 microns. The porous structure may exhibit a material thickness ranging from about 25 microns to about 75 microns and a height ranging from about 200 microns to about 300 microns.

According to another aspect of the disclosure, a therapeutic apparatus to promote healing of a wound includes a porous structure in contact with the wound for delivering micro-mechanical forces to localized areas of the wound. The porous structure comprises a film material having directional apertures formed therein. The apparatus also includes an ultrasonic horn adapted to deliver ultrasonic energy to the porous structure.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Figure 1:
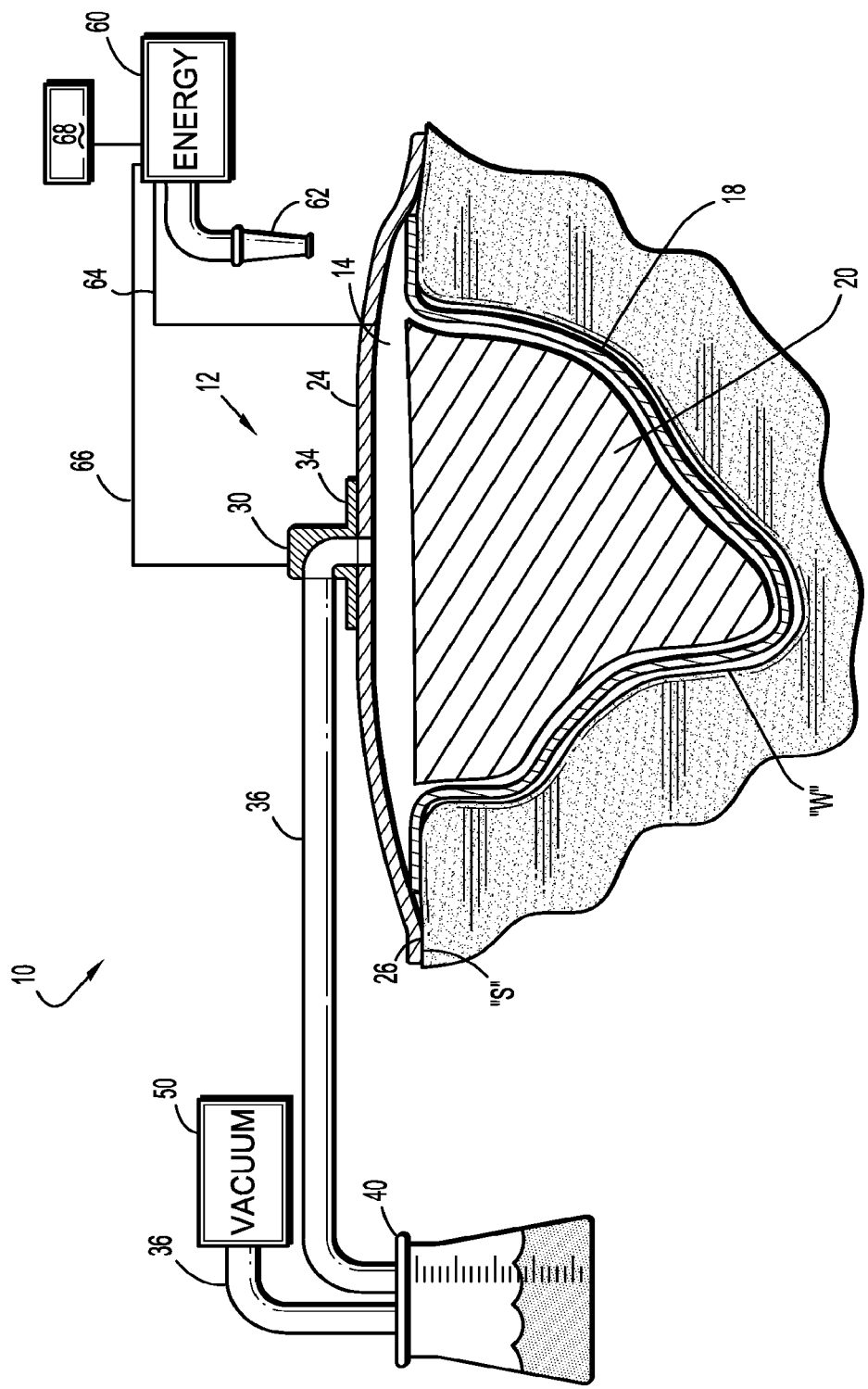
FIG. 1 is a cross sectional view of a therapeutic apparatus in accordance with the present disclosure having a porous structure in contact with the wound.
Figure 2A:
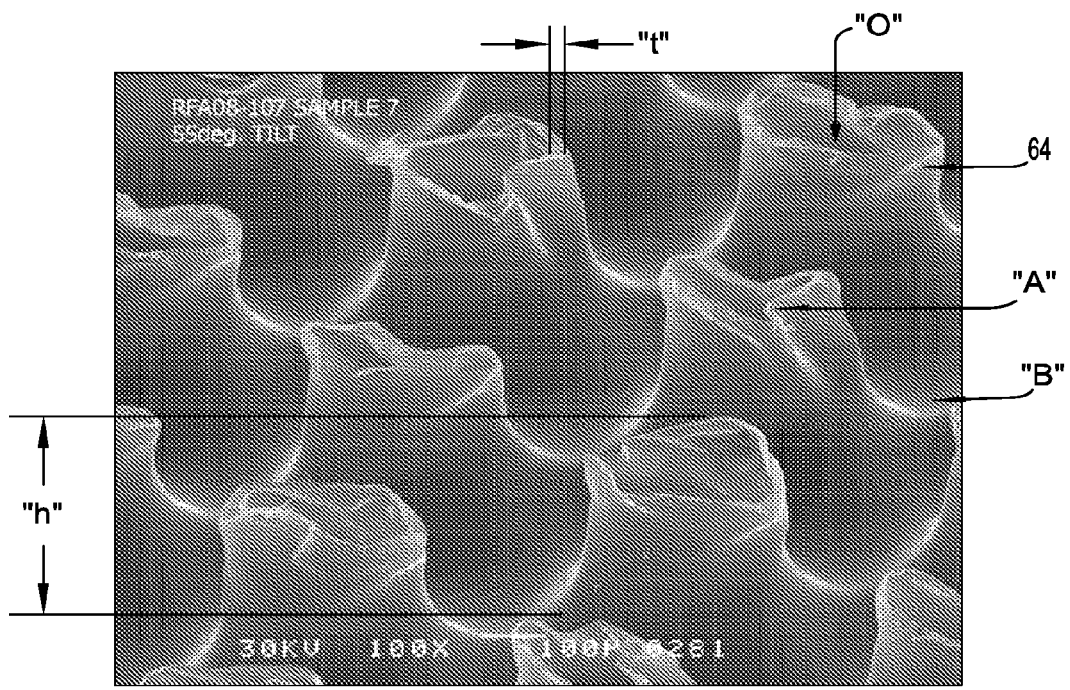
FIGS. 2A and 2B are respectively a perspective view and an orthographic view of a first portion of the porous structure of FIG. 1.
Figure 2B:
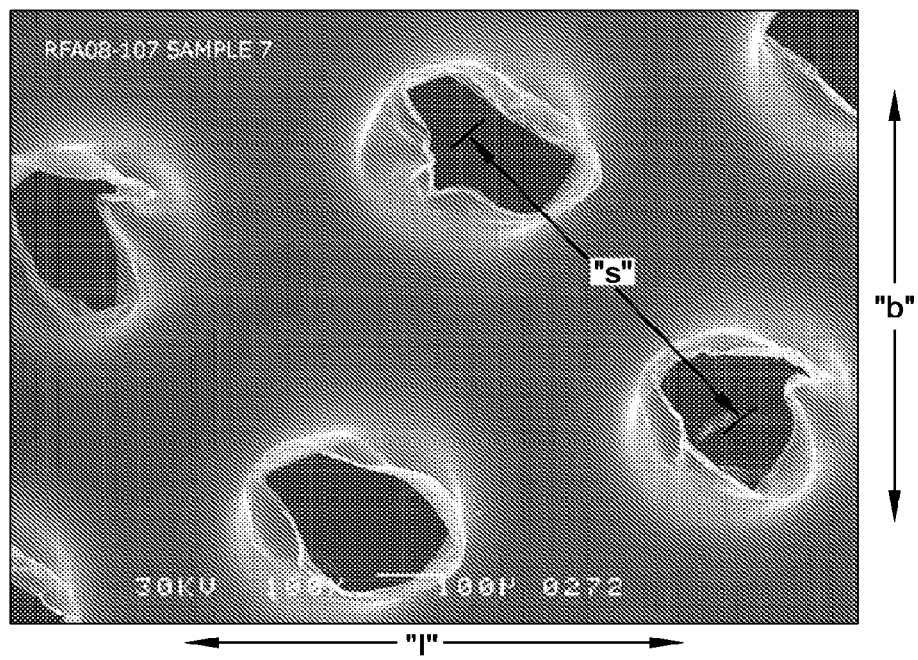
Figure 2C:
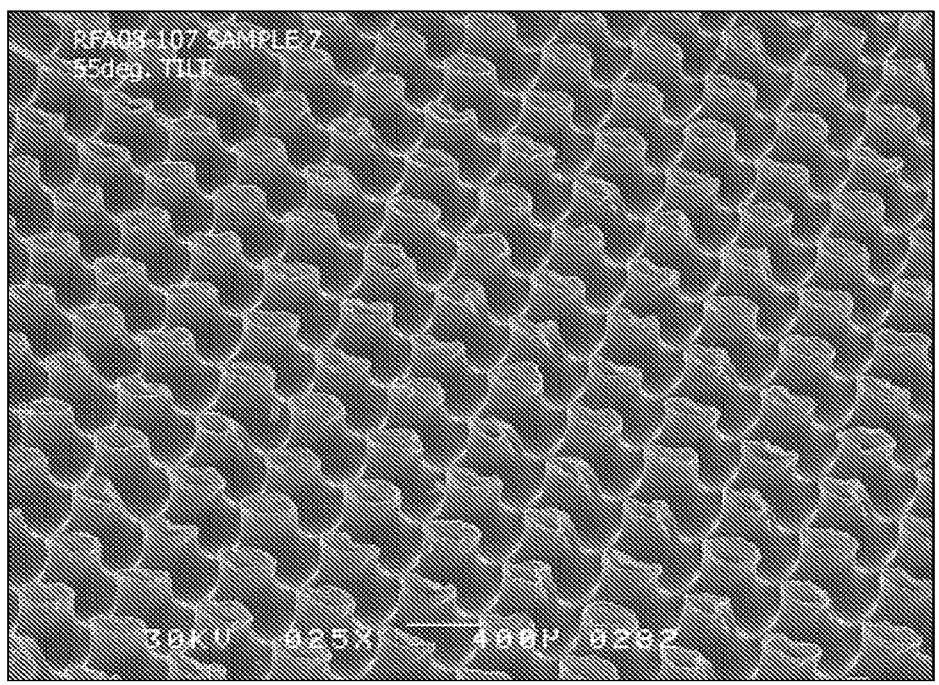
FIGS. 2C and 2D are respectively a perspective view and an orthographic view of a second portion of the porous structure of FIG. 1 that is larger than the first portion.
Figure 2D:
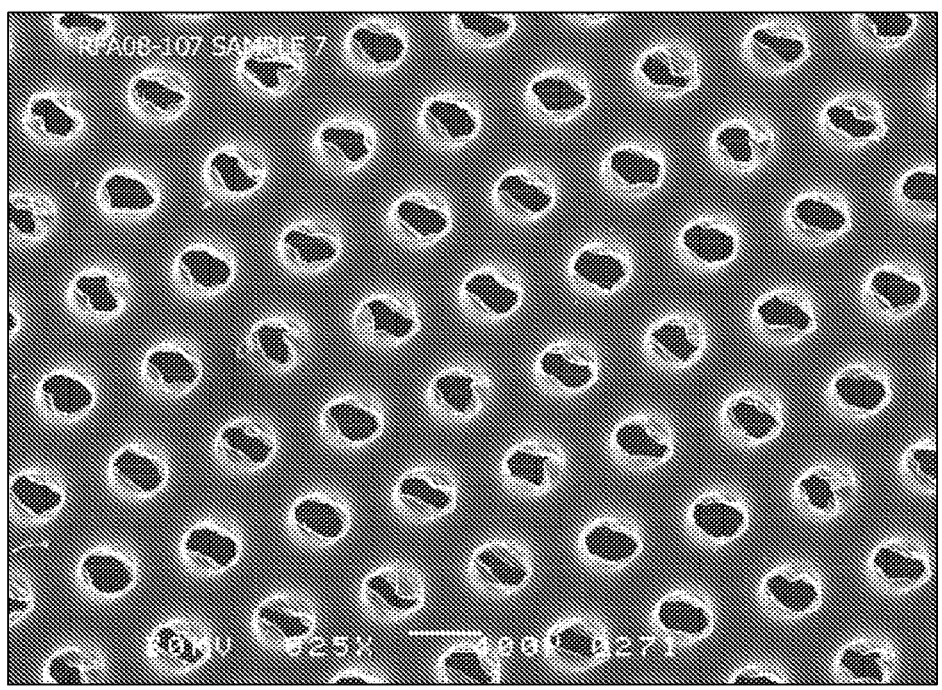

Referring initially to FIG. 1, an apparatus in accordance with the present disclosure is depicted generally as 10 for use on a wound "w" surrounded by healthy skin "s." Apparatus 10 defines a negative wound pressure therapy (NWPT) apparatus 10, which may subject the wound "w" to a negative pressure continuously, or in varying intervals depending on the nature and severity of the wound "w". One suitable NWPT apparatus is disclosed in commonly assigned U.S. patent application Ser. No. 11/516,925, filed Sep. 6, 2006, the entire content of which is hereby incorporated by reference. To facilitate the application of a negative pressure, the apparatus 10 includes a wound dressing 12 positioned relative to the wound "w" to define a reservoir 14 in which a negative pressure appropriate to stimulate healing may be maintained.

Wound dressing 12 includes a contact layer 18 positioned in direct contact with the bed of wound "w." Contact layer 18 exhibits a three-dimensional structure that is configured to deliver micro-mechanical forces to localized areas of the wound "w" while permitting the negative pressure applied to the reservoir 14 to penetrate into the wound "w." Contact layer 18 also permits exudates to be drawn from the wound "w." An appropriate contact layer 18 is discussed in greater detail below with reference to FIGS. 2A through 2D. Three-dimensional formed and apertured films such as those provided by Tredegar Film Products of Richmond, Va., may be suitable for constructing contact layer 18.

Wound filler 20 is positioned in the wound "w" over the contact layer 18 and is intended to allow wound dressing 12 to absorb and capture wound exudates, or to transport wound exudates away from the wound "w" and out of the dressing 12. Wound filler 20 may be cut to a shape that is conformable to the shape of wound "w," and may be packed up to the level of healthy skin "s," or alternatively, may overfill the wound "w." An absorbent material such as gauze, reticulated foam, or alginate fibers may be used for filler 20 to receive or transport any exudate that migrates through contact layer 18. An antimicrobial dressing, commercially available under the trademark KERLIX™ AMD offered by Tyco Healthcare Group LP (d/b/a Covidien), may be suitable for use as filler 20. To prevent adhesion to the wound "w," the filler 20 may also comprise a material configured such that any stray fibers do not tend to protrude through pores formed in contact layer 18 where they may become engulfed by newly forming granulation tissue. One particular type of material exhibiting this characteristic is formed of continuous filaments comprising either natural or man-made fibers. Continuous filaments include those relatively long strands of a synthetic material such as nylon, rayon, etc., which may offer a smooth continuous outer surface substantially free of the protruding fibrils commonly associated with natural materials such as cotton. The use of continuous filaments of a hydrophobic material such as polyolefin may permit a complete removal of filler 20 when the dressing 12 is changed without re-injuring the wound "w."

Wound dressing 12 also includes a cover layer 24. Cover layer 24 may be positioned over the wound "w" such that an adhesive on an underside of the cover layer forms a substantially fluid-tight seal with the surrounding skin "s." Thus, cover layer 24 may act as both a microbial barrier to prevent contaminants from entering the wound "w," and also a fluid barrier maintaining the integrity of vacuum reservoir 14. Cover layer 24 is preferably formed from a moisture vapor permeable membrane to promote the exchange of oxygen and moisture between the wound "w" and the atmosphere, and is preferably transparent permit a visual assessment of wound conditions without requiring removal of the cover layer 24. A transparent membrane providing a sufficient moisture vapor transmission rate (MVTR) for use as cover layer 24 is sold under the trade name POLYSKIN®II by Tyco Healthcare Group LP (d/b/a Covidien). Alternatively, cover layer 24 may comprise an impermeable membrane or a substantially rigid member.

A vacuum port 30 having a flange 34 may also be included in wound dressing 12 to facilitate connection of the wound dressing 12 to fluid conduit 36. Fluid conduit 36 defines a fluid flow path leading through the apparatus 10. The vacuum port 30 may be configured as a rigid or flexible, low-profile component, and may be adapted to receive a fluid conduit 36 in a releasable and fluid-tight manner. An adhesive on the underside of flange 34 may provide a mechanism for affixing the vacuum port 30 to the dressing 12, or alternatively flange 34 may be positioned within reservoir 14 (not shown) such that an adhesive on an upper side of the flange 34 affixes the vacuum port 30. However it is affixed to the dressing, a hollow interior of the vacuum port 30 provides fluid communication between the fluid conduit 36 and the reservoir 14. Vacuum port 30 may be provided as a pre-affixed component of dressing 12, as a component of fluid conduit 36 or entirely independently. Alternatively, vacuum port 30 may be eliminated from dressing 12 if other provisions are made for providing fluid communication with the fluid conduit 36.

Fluid conduit 36 extends from the vacuum port 30 to provide fluid communication between the reservoir 14 and collection canister 40. Any suitable conduit may be used for fluid conduit 36 including those fabricated from flexible elastomeric or polymeric materials. Fluid conduit 36 may connect to the vacuum port 30, the canister 40, or other apparatus components by conventional air tight means such as friction fit, bayonet coupling, or barbed connectors. The conduit connections may be made permanent, or alternatively a quick-disconnect or other releasable means may be used to provide some adjustment flexibility to the apparatus 10.

Collection canister 40 may comprise any container suitable for containing wound fluids. For example, a rigid bottle may be used as shown or alternatively a flexible polymeric pouch may be appropriate. Collection canister 40 may contain an absorbent material to consolidate or contain the wound drainage or debris. For example, super absorbent polymers (SAP), silica gel, sodium polyacrylate, potassium polyacrylamide or related compounds may be provided within canister 40. At least a portion of canister 40 may be transparent to assist in evaluating the color, quality or quantity of wound exudates. A transparent canister may thus assist in determining the remaining capacity of the canister or when the canister should be replaced.

Leading from collection canister 40 is another section of fluid conduit 36 providing fluid communication with vacuum source 50. Vacuum source 50 generates or otherwise provides a negative pressure to the NWPT apparatus 10. Vacuum source 50 may comprise a peristaltic pump, a diaphragmatic pump or other mechanism that is biocompatible and draws fluids, e.g. atmospheric gasses and wound exudates, from the reservoir 14 appropriate to stimulate healing of the wound "w." Preferably, the vacuum source 50 is adapted to produce a sub-atmospheric pressure in the reservoir 14 ranging between about 20 mmHg and about 500 mmHg, more preferably, about 75 mmHg to about 125 mmHg, or more preferably, about 40 mmHg to about 80 mmHg.

Apparatus 10 further includes an energy source 60 adapted to supply therapeutic energy to the contact layer 18. The application of energy to the contact layer 18 may concentrate the micro-mechanical stresses that the contact layer 18 applies to wound "w" to further stimulate healing. Energy source 60 comprises an ultrasonic generator that permits various parameters such as output power and frequency to be modulated in order to accommodate particular wound conditions. Energy source 60 is operatively coupled to an appropriate transmitter 62 to transmit energy to the contact layer 18. Here, transmitter 62 comprises an ultrasonic horn, which, in some embodiments, is substantially disconnected from the contact layer 18. The transmitter 62 is thus moveable with respect to wound "w" such that energy may be directed to targeted micro-regions of the wound. For example, the transmitter may be moved around the periphery of wound "w," which may be more responsive to the application of ultrasonic energy than interior regions of the wound. This arrangement permits energy to be supplied to contact layer 18 through cover layer 24. Alternatively, transmitter 62 of ultrasonic horn 60 and may be placed in contact with cover layer 24 or vacuum port 30 whereby the mechanical energy is transmitted through filler 20 and the exudate to contact layer 18. In some embodiments, transmitter 62 may be directly connected or mounted relative to, or within, cover layer 24 or vacuum port 30 as shown schematically by lines 64, 66, respectively. Ultrasonic horn 60 may be disposable with wound dressing 12. The ultrasonic energy applied will be within therapeutic ranges of frequency and intensity, and will vary with respect to wound type and condition of the wound. A control system 68 containing logic or software may control operation of ultrasonic horn 62 in accordance with predefined treatment modalities as selected by the user.

Ultrasonic energy is a type of mechanical energy that may be effective in transferring motion and mechanical energy directly to the contact layer 18. Alternative types of energy may affect the material properties of the contact layer 18 to cause the contact layer 18 to stretch or deform locally to concentrate the micro-mechanical stresses in the wound "w." Alternative energy types include light energy, which may be delivered through fiber optics, microwave energy, which may be delivered by an antenna, and magnetic, electrical or heat energy, which may be each be delivered by an appropriately corresponding transmitter.

Referring now to FIGS. 2A through 2D, the contact layer 18 is constructed of an apertured film having a three-dimensional structure. The structure of the film is characterized by a plurality of tapered capillary passages 50, each with a base "B" and an apex "A." A vertical distance "h" between the apex "A" of a passage 50 and the base of the passage defines a height of the film. The height "h" of the film may be many times greater than a material thickness "t" of the film, and many times smaller than a length "l" or breadth "b" of the film. For example, contact layer 18 may exhibit a material thickness "t" of from about 25 microns to about 75 microns (or approximately 1 to 3 mills), and a height "h" of from about 200 microns to about 300 microns (or approximately 8-12 mills). The film may be customized to have a length "l" and breadth "b" on the order of one to several inches to accommodate a particular wound "w."

Each tapered passage 50 includes an aperture or opening "O" located at its apex "A," while the base "B" of each passage 50 is closed. The apex "A" of each passage 50 is oriented on a male face of the film (as shown in each of FIGS. 2A through 2D) where the passages 50 are narrower than at their base "B." This arrangement may promote a unidirectional flow of wound exudates through the contact layer 18, and thus openings "O" may be described as directional apertures. Exudates may encounter the film as an array of micro-funnels in one direction and an array of collecting basins in the other. For example, orienting contact layer 18 such that a female face of the film (not shown) contacts the wound "w" allows wound exudates to be funneled away from the wound "w" to be received and transported further by filler 20. Unidirectional flow away from the wound "w" may be preferable in some instances to discourage bacteria harbored in the wound exudates from flowing back into the wound bed. Orienting the contact layer 18 with the female face in contact with the wound "w" places the relatively broader bases "B" in contact with the surface of the wound "w." Micro-mechanical forces may be applied to the wound "w" in these areas of contact as a negative pressure is applied to the reservoir 14.

Alternatively, wound contact layer 18 may be oriented such that the male face contacts the wound "w." In this orientation, the contact layer 18 may be supported only by the film material in the vicinity of the openings "O" such that a smaller surface area of the wound "w" is in contact with the film material than when compared to the opposite orientation. This arrangement permits micro-mechanical forces to be transferred to localized areas of contact with the wound "w" that may be small enough to appropriately stimulate individual cells.

Various features of the contact layer 18 may be designed to precisely control the healing of the wound "w." For example, by varying the size, shape and location of the openings "O" over the length "l" and breadth "b" of the contact layer 18, different pressures may be experienced by localized regions of the wound "w" as a particular global pressure is applied to the reservoir 14. The size of openings "O" may be selected for particular wound conditions. In some instances, wound healing may be stimulated by a film having openings "O" with a diameter of from about 50 microns to about 350 microns. Also, a spacing "s" of the openings "O" may be selected to control the application of micro-mechanical forces directed at the wound surface. The spacing "s" between adjacent openings "O" of from about 400 microns to about 800 microns may be appropriate. The shape of the openings "O" may also affect healing. The shape of the openings "O" depicted in FIGS. 2A through 4D is generally round, but oblong or asymmetrical shapes are also contemplated. These shapes may create stress concentrations to further localize the application of micro-mechanical forces to the wound "w."

Material properties of contact layer 18 such as a film elasticity, material hardness, composition and chemistry may be selected to precisely control aspects of healing. Additionally, agents such as hydrogels and medicaments may be bonded or coated to the contact layer 18 to reduce bioburden in the wound, promote healing and reduce pain associated with changes or removal of the dressing 12. Medicaments include, for example, antimicrobial agents, growth factors, antibiotics, analgesics, and the like. Furthermore, when an analgesic is used, the analgesic could include a mechanism that would allow the release of that agent prior to dressing removal or change.

Although the foregoing disclosure has been described in some detail by way of illustration and example, for purposes of clarity or understanding, it will be obvious that certain changes and modifications may be practiced within the scope of the appended claims.

What is claimed is:

1. A therapeutic apparatus to promote healing of a wound comprising:
   a wound cover for defining a reservoir over a wound in which a negative pressure may be maintained by forming a substantially fluid-tight seal around the wound;
   a vacuum source configured to be in fluid communication with the reservoir, the vacuum source suitable for providing an appropriate negative pressure to the reservoir to stimulate healing of the wound; and
   a three-dimensional film material configured to be in contact with the wound, the three-dimensional film material having a plurality of passages defined between a male face and an opposite female face thereof;
   wherein the three-dimensional film material is configured to be positioned such that the male face is in contact with the wound, and wherein each of the passages includes an aperture at an apex oriented on the male face and a base oriented on the female face.

2. The apparatus according to claim 1, further comprising a wound filler positioned within the reservoir.

3. The apparatus according to claim 1, further comprising a port in communication with the wound cover, the port comprising a flange.

4. The apparatus according to claim 3, wherein the port is configured to provide fluid communication between a fluid conduit and the reservoir, wherein the fluid conduit is in fluid communication with the vacuum source and configured to provide negative pressure to the reservoir.

5. The apparatus according to claim 1, further comprising an energy source and a transmitter adapted to deliver energy to the three-dimensional film material.

6. The apparatus according to claim 5, wherein the transmitter comprises an ultrasonic horn.

* * * * *